United States Patent
Nabatame

(10) Patent No.: US 7,215,733 B2
(45) Date of Patent: May 8, 2007

(54) X-RAY COMPUTED TOMOGRAPHY APPARATUS

(75) Inventor: Takeo Nabatame, Otawara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 73 days.

(21) Appl. No.: 11/186,871

(22) Filed: Jul. 22, 2005

(65) Prior Publication Data

US 2006/0018425 A1     Jan. 26, 2006

(30) Foreign Application Priority Data

Jul. 23, 2004    (JP) .............................. 2004-216308

(51) Int. Cl.
*G01N 23/00*    (2006.01)

(52) U.S. Cl. .......................... 378/16; 378/110; 378/112

(58) Field of Classification Search .............. 378/4–20, 378/108–112
See application file for complete search history.

(56) References Cited

U.S. PATENT DOCUMENTS 6,141,398 A * 10/2000 He et al. ...................... 378/4
6,490,337 B1 * 12/2002 Nagaoka et al. .............. 378/20
6,754,301 B2    6/2004 Horiuchi ....................... 378/16
6,956,929 B2 * 10/2005 Wolf et al. .................. 378/109

FOREIGN PATENT DOCUMENTS

JP     2003-70779     3/2003

* cited by examiner

*Primary Examiner*—Edward J. Glick
*Assistant Examiner*—Jurie Yun
(74) *Attorney, Agent, or Firm*—Oblon, Spivak, McClelland, Maier & Neustadt, P.C.

(57) ABSTRACT

A plurality of region-specific areas are set on a scanogram, and an image SD value is set for each region-specific area. A tube current calculating unit calculates a tube current value at each position on the basis of a tube current pattern in a tube current pattern storage unit, an image SD value for each region-specific area, and a CT value at each position on the scanogram in each region-specific area. A scan controller controls X-ray emission in accordance with a calculated tube current value at each position.

15 Claims, 8 Drawing Sheets

FIG. 5

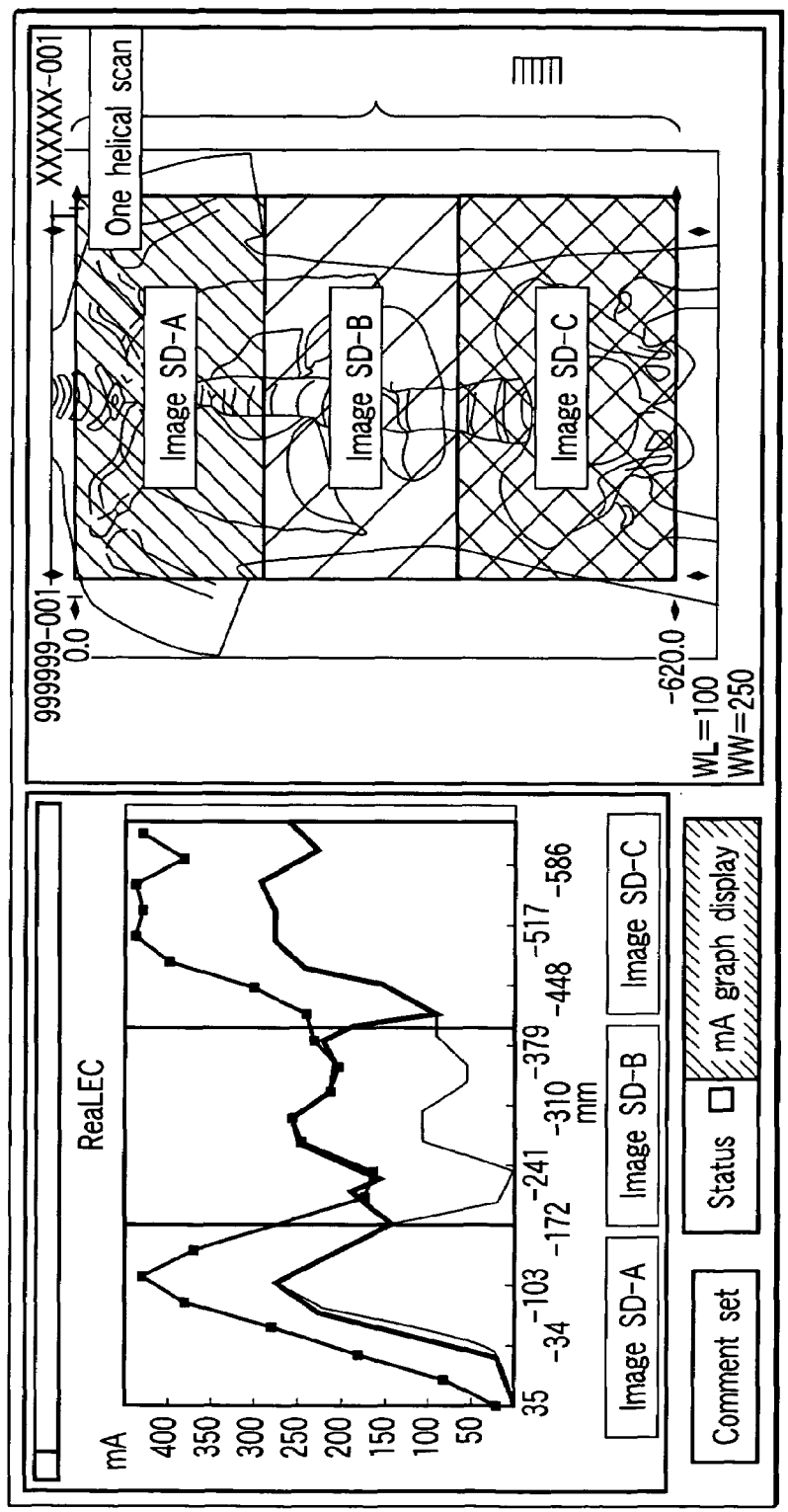
F I G. 6A

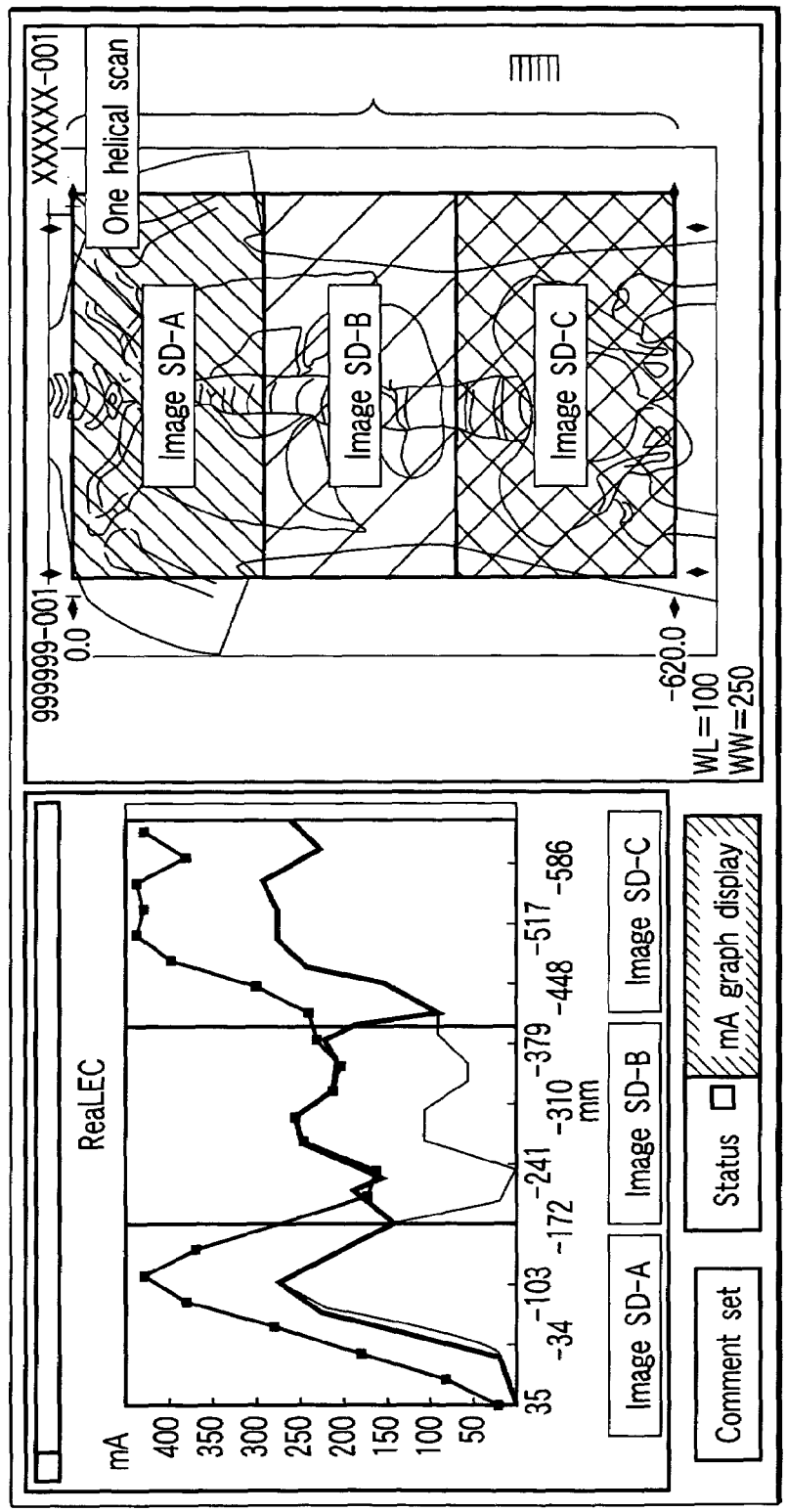
F I G. 6B

X-RAY COMPUTED TOMOGRAPHY APPARATUS

CROSS-REFERENCE TO RELATED APPLICATIONS

This application is based upon and claims the benefit of priority from prior Japanese Patent Application No. 2004-216308, filed Jul. 23, 2004, the entire contents of which are incorporated herein by reference.

BACKGROUND OF THE INVENTION

1. Field of the Invention

The present invention relates to an X-ray computed tomography apparatus which can set appropriate tube currents (mA) for different regions upon one helical scan by designating an image SD (Standard Deviation) for each region.

2. Description of the Related Art

As is known, an X-ray computed tomography apparatus is designed to obtain an image (tomographic image) by calculating (reconstructing) the X-ray absorption coefficient of tissue such as an organ on the basis of the amount of X-rays absorbed in a subject to be examined as an index called a CT value with reference to the X-ray absorption coefficient of water.

A reconstructed image inevitably contains image noise. Image noise is typically defined with reference to a variation in the CT value of a homogeneous phantom image as a standard deviation, which is generally referred to as an image SD. In order to make diagnosis by observing a reconstructed image, e.g., to discriminate a shadow on the image as noise or a tumor, the image SD unique to the image must be considered.

FIG. 1 is a view for explaining a technique called conventional real EC. Conventional real EC is used to automatically calculate a tube current (mA) for a designated image SD from the CT value of a scanogram at a corresponding position. This technique determines a tube current so as to obtain the image SD designated at each position. Therefore, images with uniform image quality can be acquired regardless of the physiques of patients. In addition, the exposure to X-rays of a subject can be reduced as compared with a case wherein data is acquired with a constant tube current.

There is a strong tendency that such an image SD depends on the transmission dose of X-rays which is mainly determined by the relationship between a tube current and a subject to be examined. For this reason, the image SD for obtaining clinically required image quality varies depending on an imaging region, a tumor as a diagnosis target, or the like. In consideration of such a general situation, an image SD is preferably set for each imaging region in a sequence in terms of a reduction in the exposure to X-rays.

In a conventional system, however, an image SD cannot be set for each imaging region in a sequence. For this reason, when an image SD is to be changed for each imaging region so as to further reduce the exposure to X-rays, a helical scan is dividedly executed, and an individual image SD is designated for each scan. This increases the time and labor for imaging. In addition, the X-ray emission area must be set to be larger than the reconstruction range in each scan, and hence this may rather increase the exposure to X-rays.

BRIEF SUMMARY OF THE INVENTION

In the conventional system, however, an image SD cannot be set for each imaging region in a sequence. For this reason, when an image SD is to be changed for each imaging region in order to further reduce the exposure to X-rays, a helical scan is dividedly executed, and a unique image SD is designated for each scan. This increases the time and labor required for imaging. In addition, an X-ray emission area in each scan must be wider than a reconstruction range. This may rather increase the exposure to X-rays.

The present invention has been made in consideration of the above situation, and has as its object to provide an X-ray computed tomography apparatus which can shorten the imaging time and reduce the operation load on a person who performs imaging while reducing the exposure to X-rays of a subject to be examined, by allowing to set an image SD for each imaging region in an imaging sequence.

According to an aspect of the present invention, there is provided an X-ray computed tomography apparatus which comprises: an imaging unit which acquires projection data in an arbitrary range in a body axis direction of a subject to be examined by continuously moving a table-top on which the subject is placed and continuously rotating around the subject while exposing X-rays using an X-ray tube; an image quality level setting unit which sets unique image quality levels for a plurality of areas corresponding to each region of a CT image of the subject; a calculating unit which calculates an X-ray condition corresponding to a plurality of positions in the each area on the basis of the image quality level; and a control unit which controls the imaging unit so as to acquire projection data continuously in the each area by exposing X-rays using the X-ray tube in accordance with the X-ray condition, which are obtained by the calculation.

According to another aspect of the present invention, there is provided an X-ray computed tomography apparatus which comprises: an imaging unit which acquires projection data in an arbitrary range in a body axis direction of a subject to be examined by continuously moving a table-top on which the subject is placed and continuously rotating around the subject while exposing X-rays using an X-ray tube; a setting unit which sets a unique image SD value for each area obtained by dividing a scanogram of the subject into a plurality of areas corresponding to each region; a storage unit in which first X-ray condition information with each CT value being associated with each X-ray condition is stored for each image SD value; a calculating unit which calculates an X-ray condition corresponding to a plurality of positions in the each area on the basis of a CT value of the scanogram at each of the plurality of positions in the each area, the set image SD value for the each area and the first X-ray condition information; and a control unit which controls the imaging unit so as to acquire projection data continuously in the each area by exposing X-rays using the X-ray tube in accordance with the X-ray condition, which are obtained by the calculation.

BRIEF DESCRIPTION OF THE SEVERAL VIEWS OF THE DRAWING

Figure 5:
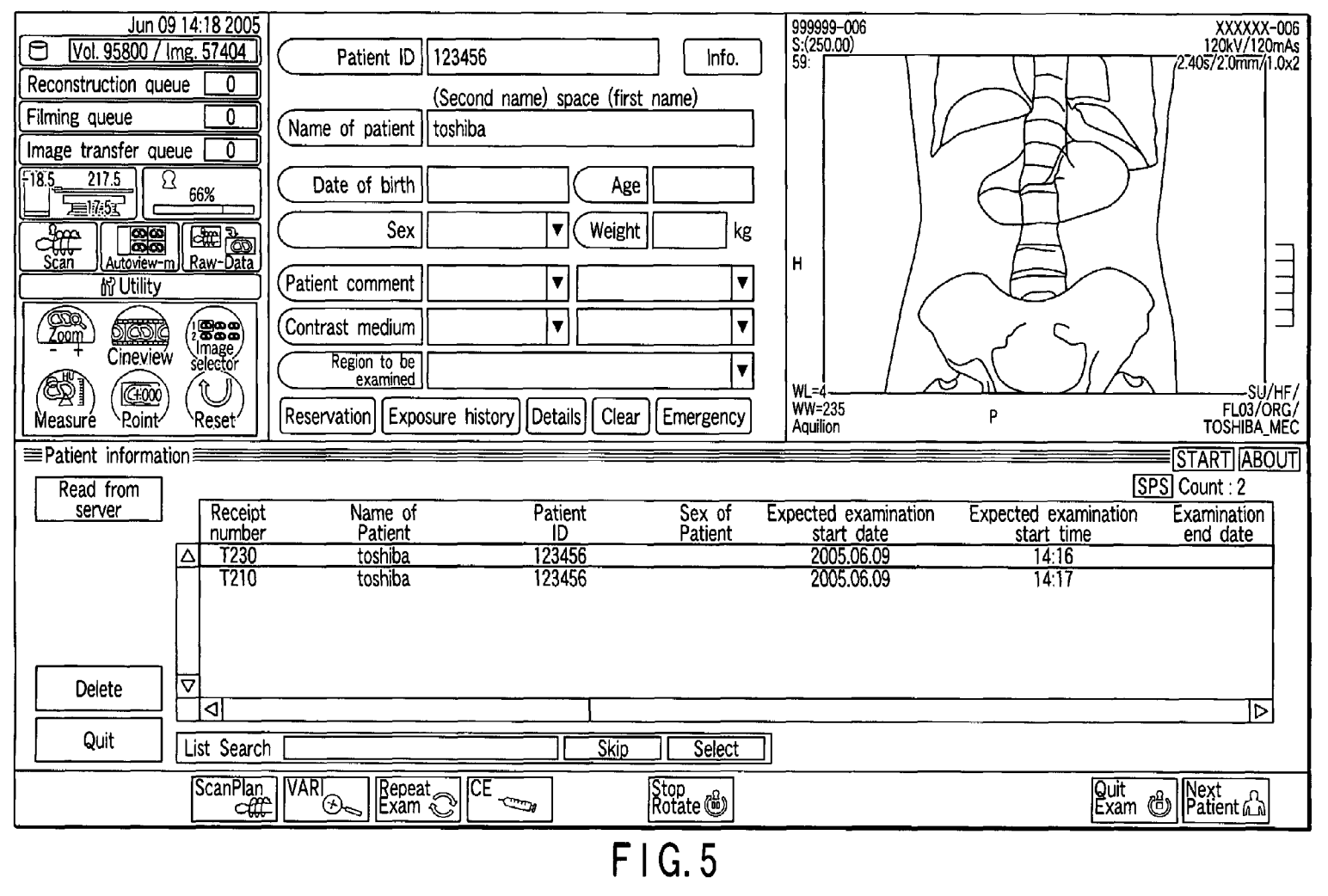

FIG. 5 is a view for explaining the inputting of an image SD for each region-specific imaging area through an RIS;

FIGS. 6A and 6B are views each showing each region-specific imaging area (on the right side in FIG. 6A or 6B) whose size is determined on a scanogram, and a graph (on the left side in FIG. 6A or 6B) of tube current values determined in accordance with an image SD value for each region-specific imaging area.

DETAILED DESCRIPTION OF THE INVENTION

Figure 1:
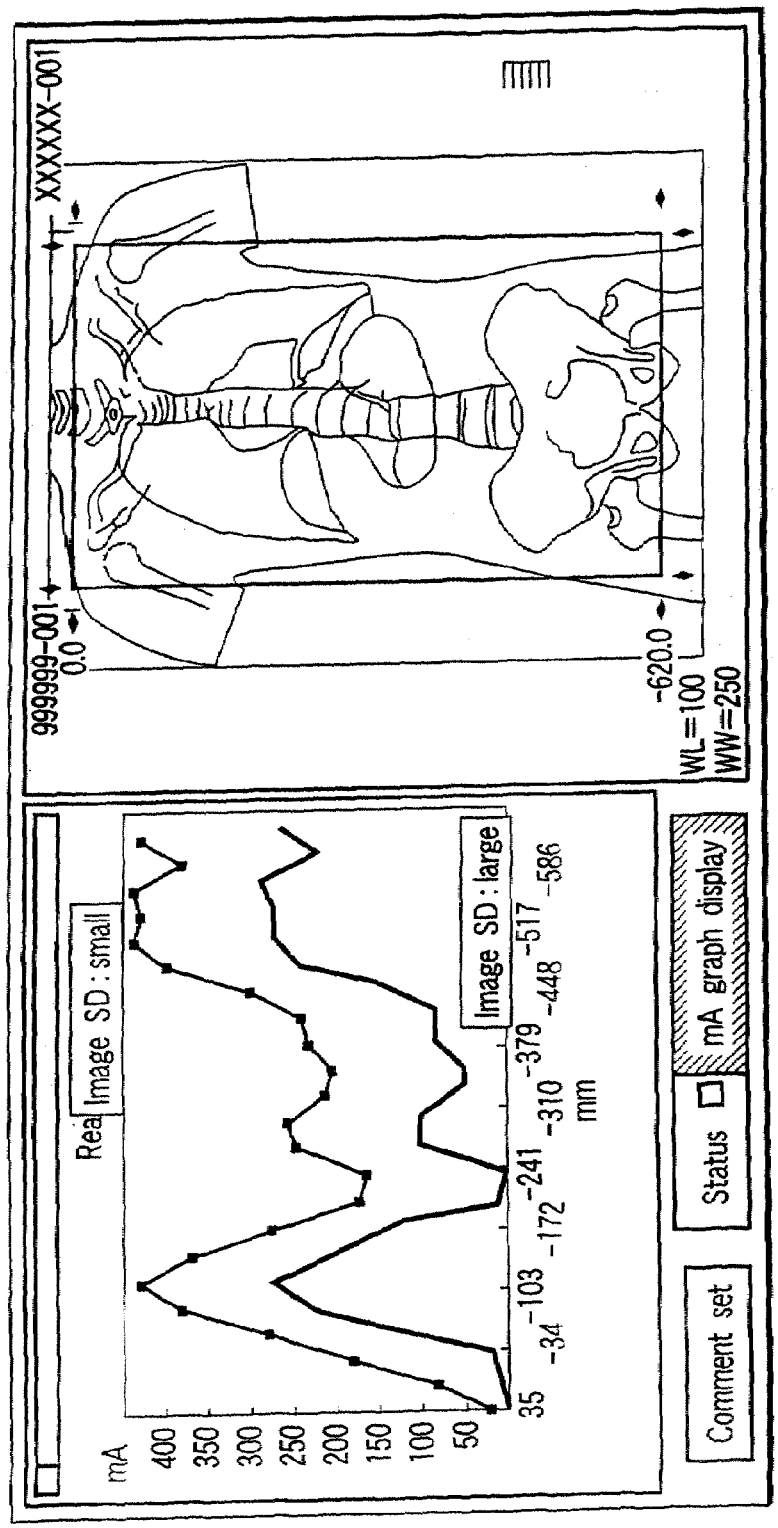
FIG. 1 is a view for explaining a technique called conventional real EC.

An embodiment of the present invention will be described with reference to the views of the accompanying drawing. In the following description, the same reference numerals denote constituent elements having almost the same functions and arrangements, and a repetitive description thereof will be made only when required.

An embodiment of an X-ray computed tomography apparatus according to the present invention will be described below with reference to the views of the accompanying drawing. Note that X-ray computed tomography apparatuses include various types of apparatuses, e.g., a rotate/rotate-type apparatus in which an X-ray tube and X-ray detector rotate together around a subject to be examined, and a stationary/rotate-type apparatus in which many detection elements arrayed in the form of a ring, and only an X-ray tube rotates around a subject to be examined. The present invention can be applied to either type. In this case, the rotate/rotate type, which is currently the mainstream, will be exemplified.

In order to reconstruct one-slice tomographic image data, projection data corresponding to one rotation around a subject to be examined, i.e., about 360°, is required, or (180°+view angle) projection data is required in the half scan method. The present invention can be applied to either of these reconstruction schemes. The former scheme will be exemplified here.

As mechanisms of converting incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor by X-rays and movement of the electron-hole pairs to an electrode, i.e., a photoconductive phenomenon. As an X-ray detection element, either of these schemes can be used. In this case, the former type, i.e., the indirect conversion type, will be exemplified.

Recently, with advances toward the commercialization of a so-called multi-tube type X-ray computed tomography apparatus having a plurality of pairs of X-ray tubes and X-ray detectors mounted on a rotating frame, related techniques have been developed. The present invention can be applied to both a conventional single-tube type X-ray computed tomography apparatus and a multi-tube type X-ray computed tomography apparatus. The single-tube type X-ray computed tomography apparatus will be exemplified here.

Figure 2:
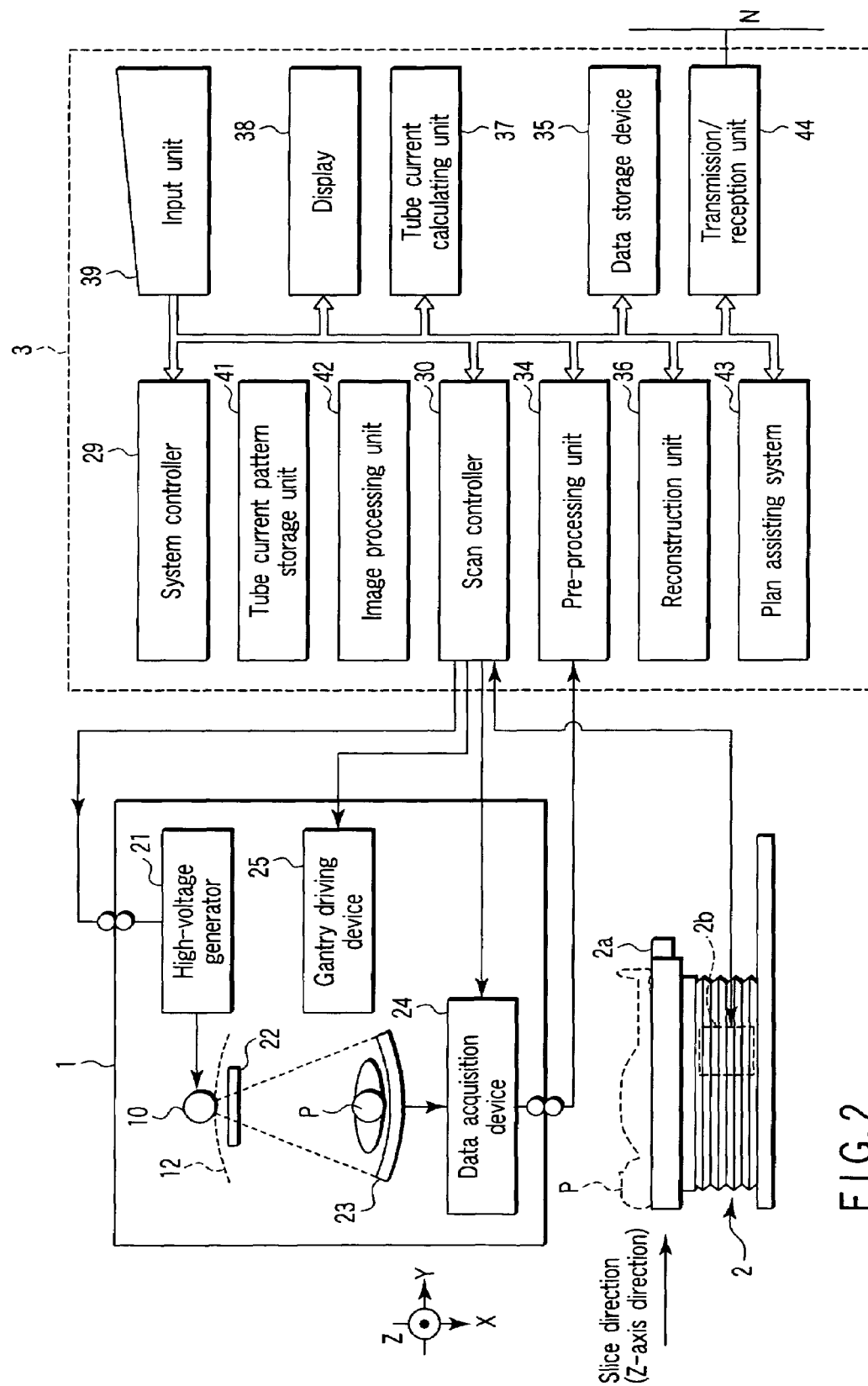
FIG. 2 is a block diagram showing the arrangement of an X-ray computed tomography apparatus according to this embodiment.

FIG. 2 is a block diagram showing the arrangement of an X-ray computed tomography apparatus according to this embodiment. The X-ray computed tomography apparatus comprises a gantry 1, bed 2, and computer system 3.

The gantry 1 is designed to acquire projection data associated with a subject P to be examined, and comprises an X-ray tube 10, rotating frame 12, high-voltage generator 21, slit 22, X-ray detector 23, data acquisition device 24, and gantry driving device 25.

The rotating frame 12 is a ring which is rotated/driven about the Z-axis, on which the X-ray tube 10 and X-ray detector 23 are mounted. An opening portion is formed in the central portion of the rotating frame 12. The subject P which is placed on a top 2a of the bed 2 is inserted in the opening portion.

The gantry driving device 25 rotates/drives the rotating frame 12. With this rotating/driving operation, the X-ray tube 10 and X-ray detector 23 helically rotate about the body axis of the subject while facing each other.

The slit 22 is provided in the opening portion between the X-ray tube 10 and the rotating frame 12, and shapes the X-ray beam exposed from the X-ray tube 10 into a conical shape (quadrangular pyramidal shape) or fan-beam shape in accordance with a slice thickness.

The X-ray tube 10 is a vacuum tube which generates X-rays, and is provided on the rotating frame 12. Power (a tube current or tube voltage) required for the emission of X-rays is supplied from the high-voltage generator 21 to the X-ray tube 10 through a slip ring (not shown). The X-ray tube 10 accelerates electrons using the applied high voltage and causes the electrons to impinge on a target, thereby applying X-rays to the subject placed in an effective field of view FOV.

The high-voltage generator 21 is a device which supplies the power required for the emission of X-rays to the X-ray tube 10 through a slip ring (not shown), and comprises a high-voltage transformer, filament heating converter, rectifier, high-voltage switch, and the like.

The X-ray detector 23 is a detector system which detects X-rays transmitted through the subject, and is mounted on the rotating frame 12 facing the X-ray tube 10. The X-ray detector 23 is a single slice type detector or multi-slice type detector, in which a plurality of detection elements comprising combinations of scintillators and photodiodes are arrayed in a form corresponding to each type. The X-ray detector 23 as a single slice type detector has an element array of, for example, 916 X-ray detection elements, each having a 0.5 mm×0.5 mm square light-receiving surface, arranged in a line along the channel direction. The X-ray detector 23 as a multi-slice type detector has, for example, 40 element arrays arranged side by side in the slice direction.

The data acquisition device 24 generally called a DAS (Data Acquisition System) converts a signal output from the X-ray detector 23 for each channel into a voltage signal, amplifies it, and further converts it into a digital signal. This data (raw data) is loaded into the computer system 3 placed outside the gantry. A pre-processing unit 34 of the computer system 3 performs correction processing such as sensitivity correction for the raw data output from the data acquisition device 24 and outputs the resultant projection data. This projection data is sent to a data storage device 35 of the computer system 3 to be stored.

The bed 2 is equipped with a top driving unit 2b for moving the top 2a in the direction of the long axis (parallel to the rotation axis) of the top. The top driving unit 2b has a top position detecting unit such as a rotary encoder for detecting the position of the top 2a.

The computer system 3 comprises a system controller 29, a scan controller 30, the pre-processing unit 34, the data storage device 35, a reconstruction unit 36, a tube current calculating unit 37, a display 38, an input unit 39, a tube current correcting unit 40, a tube current pattern storage unit 41, a parameter storage unit 42, a plan assisting system 43, and a transmission/reception unit 44.

The system controller 29 systematically controls signal processing, image processing, and the like executed by the computer system 3.

A scan controller 30 performs systematic control associated with imaging processing. For example, in imaging processing, the scan controller 30 stores scan conditions such as a pre-input slice thickness in an internal memory, and controls the feed amounts and feed speeds of the high-voltage generator 21, the bed driving unit (not shown), the gantry driving device 25, and the top 2a of the bed 2 in the body axis direction, and the rotational speed, rotation pitch, X-ray emission timing, and the like of the X-ray tube 10 and X-ray detector 23 on the basis of scan conditions automatically selected by a patient ID or the like (or scan conditions directly set through the input unit 39 in a manual mode), thereby applying an X-ray cone beam or X-ray fan beam to a desired imaging region of the subject in many directions and performing imaging processing for an X-ray CT image.

The pre-processing unit 34 receives raw data from the data acquisition device 24 through a noncontact data transmission device (not shown), and executes sensitivity correction and X-ray intensity correction. The 360° raw data having undergone various kinds of correction processing is temporarily stored in the data storage device 35. Note that the raw data having undergone the pre-processing performed by the pre-processing unit 34 will be called "projection data".

The data storage device 35 stores image data such as raw data, projection data, scanogram data, and tomographic data, a program for examination planning, and the like.

The reconstruction unit 36 is equipped with a plurality of kinds of reconstruction methods, and reconstructs image data by the reconstruction method selected by the operator. The plurality of types of reconstruction methods include, for example, the fan beam reconstruction method (also called the fan beam convolution/back projection method), the Feldkamp method, and the cone beam reconstruction method. The Feldkamp method is used as a reconstruction method when projection rays obliquely intersect a reconstruction plane. The Feldkamp method is an approximate image reconstruction method in which convolution processing is performed by regarding data as a fan projection beam on the premise that the cone angle is small, and back projection processing is performed along a ray in a scan. The cone beam reconstruction method is a method which suppresses cone angle errors more than the Feldkamp method.

In this method, projection data is corrected in accordance with the angle of a ray with respect to a reconstruction plane.

An image processing unit 42 performs image processing for display, e.g., window conversion and RGB processing, for reconstructed image data generated by the reconstruction unit 36, and outputs the resultant data to the display 38. The image processing unit 42 generates a so-called pseudo three-dimensional image such as a tomographic image of an arbitrary slice, a projection image from an arbitrary direction, or a three-dimensional surface image, and outputs it to the display 38.

The plan assisting system 43 has a function required to interactively guide the determination of a scan plan by the operator. For example, the plan assisting system 43 constructs a window for prompting the operator to input items such as patient information, examination purpose, and examination region, and displays the window. When the operator inputs necessary items in the window, the plan assisting system 43 generates a corresponding scan plan, constructs a window for prompting the operator to select and correct the plan, and displays the window. In the scan plan window, patient information, gantry information, and a scanogram are displayed on the upper part, and the details of scan conditions are displayed on the lower part. The scan conditions include a plurality of items, e.g., the start and end positions of a helical scan synchronized with the frame lines of the scanogram, a scan mode, a scan count, a tube voltage (kV), a tube current (mA), a scan speed (the numerical value in the parentheses indicates an imaging time) representing the time required for the X-ray tube 10 to make one rotation, a reconstruction mode, an imaging field of view (FOV), and a helical pitch representing the distance that the top moves at the scan speed.

For the tube current (mA) item in the scan plan window, a box in which a numerical value is directly input as a tube current value and a pull-down menu are prepared. As the choices of the pull-down menu, "automatic" (Auto) is prepared as well as a plurality of tube current values. This automatic setting for a tube current value is defined as a function of, when the operator designates an image SD as an index representing image quality, automatically setting a tube current value necessary to realize the designated image SD on the system side. In setting this image SD, a method of directly designating an SD value, a method of designating a name or the like associated with an SD value, or the like may be used.

The plan assisting system 43 has a function of dividing the scanogram displayed in the scan plan window into a plurality of areas, and setting an image SD for each area. This function will be described in detail later.

The tube current pattern storage unit 41 stores information (tube current pattern information) with a correspondence pattern of each CT value and each tube current value being set for each image SD value. A tube current pattern is acquired in advance by using, for example, a human body or human body simulation phantom (e.g., a water phantom). When the operator selects a desired image SD for each region-specific area, a tube current pattern corresponding to the selected image SD is selected as will be described later.

The tube current calculating unit 37 calculates a tube current value necessary to realize each image SD set by the plan assisting system 43 for each area on the scanogram on the basis of the tube current patterns in the tube current pattern storage unit 41. In practice, the tube current calculating unit 37 is a ROM, which receives a necessary parameter and outputs a calculated tube current value corresponding to the parameter. There has been currently available a technique called modulation, in which a subject to be examined is regarded as an ellipsoid, and X-ray conditions are changed depending on the thickness of the subject in the emission direction. When such modulation is to be executed, the tube current calculating unit 37 calculates a tube current value on the basis of a tube current pattern in the tube current pattern storage unit 41 which is defined to execute modulation.

When a temporal change in tube current value calculated by the tube current calculating unit 37 exceeds the operation limit value of the X-ray computed tomography apparatus, the tube current correcting unit 37 corrects the calculated tube current value to make it fall within the operation limit value. Assume that different image SDs are designated for adjacent region-specific imaging areas. In this case, in order to realize the image SDs designated for the respective areas, a temporal change in tube current value may exhibit a steep slope at the boundary between the region-specific imaging regions and exceed the operation limit value of the X-ray computed tomography apparatus. In such a case, the tube current correcting unit 40 corrects the tube current value so as to make it fall within the operation limit value at the boundary between the region-specific imaging areas.

The display 38 is an output device which displays a CT image such as a computed tomographic image or scanogram input from the image processing unit 42. In this embodiment, a CT image is defined as an "image generated on the basis of each CT value in an imaging region which is acquired by an X-ray computed tomography apparatus". In this case, a CT value represents the X-ray absorption coefficient of a substance as a value relative to a reference substance (e.g., water). The display 38 displays a scan plan window or the like realized by the plan assisting system 43.

The input unit 39 is a device which includes a keyboard, various switches, a mouse, and the like and can input various kinds of scan conditions such as a slice thickness and slice count through the operator.

The transmission/reception unit 44 transmits/receives image data, patient information, and the like to/from another apparatus through a network N. The transmission/reception unit 44, in particular, receives information associated with imaging of the subject (patient information, a diagnosis region, the image SD desired by a doctor in charge, and the like) from an RIS (Radiology Information System) connected to the network N.

(Imaging-Region-Specific Image Quality Level Setting Function)

The imaging-region-specific image quality level setting function of this X-ray computed tomography apparatus will be described next. This function allows to set an image quality level for each imaging region in an imaging sequence. When an image quality level is set for each imaging region, an X-ray condition necessary to realize each image quality is calculated for each imaging region, and control associated with X-ray emission is executed in accordance with the condition. In this case, the X-ray condition means a physical quantity influencing X-rays to be exposed, e.g., an X-ray tube current value or X-ray tube voltage value. In this embodiment, for the sake of a concrete description, assume a case wherein an X-ray tube current value is calculated as an X-ray condition.

In this embodiment, the concept "region-specific area" is introduced to allow image quality level setting for each imaging region. This "region-specific area" is set on a CT image by using the plan assisting system 43, and is used to divide the CT image into a plurality of areas in the body axis direction of the subject.

In this embodiment, for the sake of a concrete description, assume that an image SD is set as an image quality level, and a CT image on which region-specific areas are set by using the plan assisting system 43 is a scanogram acquired before real imaging (acquisition of a diagnosis image by a helical scan).

When a plurality of region-specific areas are set on a scanogram, an image SD is set for each region-specific area in a predetermined window using the plan assisting system 43. The tube current calculating unit 37 selects a tube current pattern corresponding to the set image SDs, and calculates a tube current for each slice position along the body axis direction on the basis of the CT value of the scanogram in each region-specific area. In real imaging, the high-voltage generator 21 is controlled in accordance with the tube currents obtained by this calculation, and X-ray emission is executed.

(Operation)

A series of imaging operations by this X-ray computed tomography apparatus will be described next, with particular emphasis on image SD setting for each imaging region.

Figure 3:
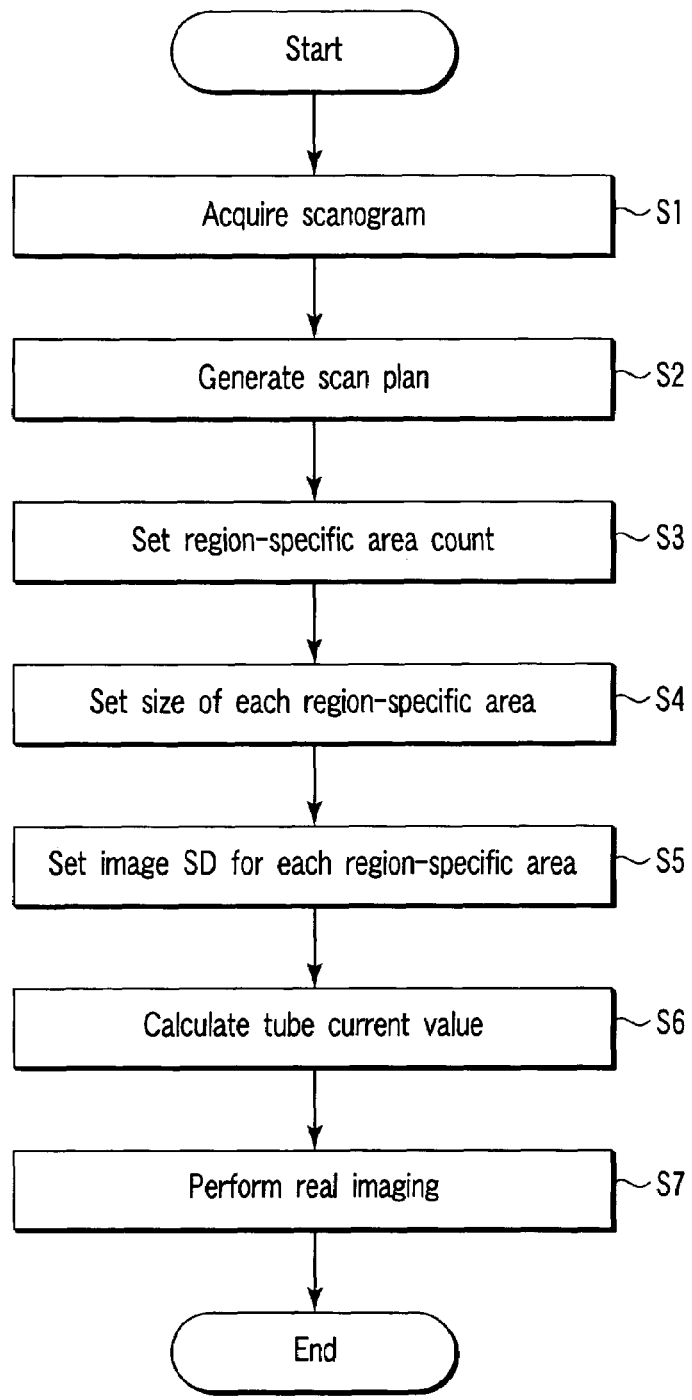
FIG. 3 is a flowchart showing the flow of processing executed in the imaging operation of this X-ray computed tomography apparatus.

FIG. 3 is a flowchart showing the flow of processing to be executed in the imaging operation of this X-ray computed tomography apparatus. As shown in FIG. 3, first of all, before real imaging is performed by a helical scan, a scanogram is acquired (step S1). When the operator inputs necessary items such as patient information, an examination purpose, and an examination region by using the plan assisting system 43, a scan plan is generated (step S2).

A region-specific imaging area count is set in a predetermined window using the plan assisting system 43 (step S3). For the sake of a concrete description, assume that in this case, the region-specific imaging area count is set to "3".

Figure 4:
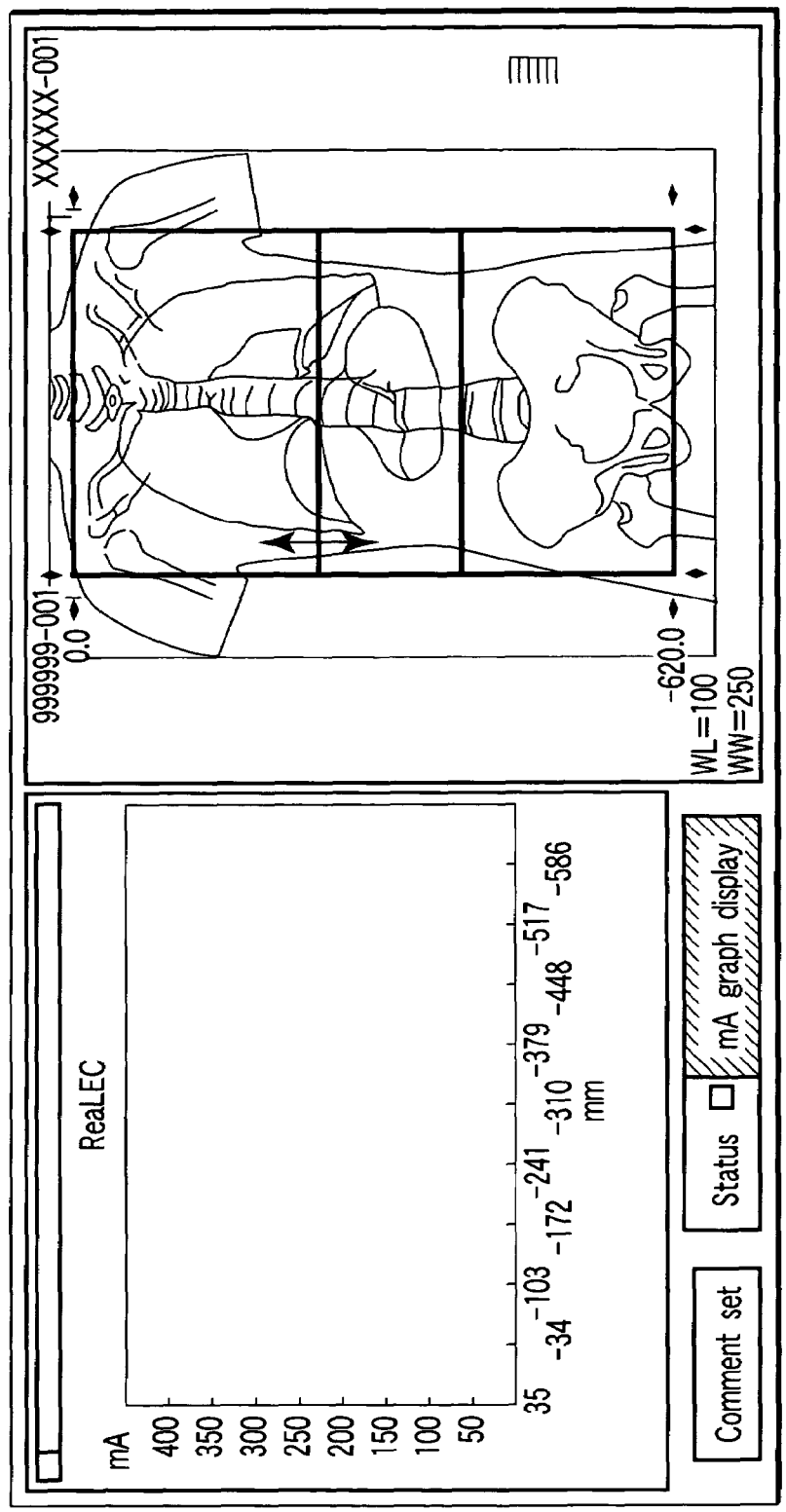
FIG. 4 is a view showing three region-specific imaging areas (on the right side in FIG. 4) set on a scanogram by setting a region-specific imaging area count, and a coordinate system (on the left side in FIG. 4) with the abscissa representing the slice position along the body axis direction and the ordinate representing the tube current value.

When a region-specific imaging area count is set, region-specific imaging areas corresponding to the count are displayed on a scanogram. FIG. 4 is a view showing three region-specific imaging areas (on the right side in FIG. 4) set on a scanogram by setting the region-specific imaging area count to "3", and a coordinate system (on the left side in FIG. 4) with the abscissa representing the slice position along the body axis direction and the ordinate representing the tube current value. Note that the sizes of the three region-specific imaging areas set on the scanogram in this stage are determined in accordance with initial settings.

As indicated by the right side in FIG. 4, the respective region-specific imaging areas are set to desired sizes by moving the boundary lines between the region-specific imaging areas or the outer frames of the respective region-specific imaging areas with the mouse (step S4).

An image SD value is set for each region-specific imaging area (step S5). This image SD setting for each region-specific imaging area can be done on the basis of information acquired by the transmission/reception unit 44 through the network N, as well as by inputting information from the input unit 39. Assume that with respect to a patient with the ID number "123456", two different imaging orders (e.g., receipt numbers T230 and T210) are received from the transmission/reception unit 44 through the RIS. In this case, the tube current calculating unit 37 sets an image SD value for each region-specific imaging area on the basis of the imaging region and image SD designated in each imaging order. Note that the two imaging orders received through the RIS are integrated into one imaging sequence as needed from the viewpoint of minimizing the imaging count.

The tube current calculating unit 37 calculates a tube current value necessary to realize each image SD set by the plan assisting system 43 for each region-specific imaging area on the scanogram on the basis of the tube current pattern in the tube current pattern storage unit 41 (step S6).

FIG. 6A shows each region-specific imaging area (on the right side in FIG. 6A) whose size is determined on a scanogram and a graph (the thick lines on the left side shown in FIG. 6A) indicating tube current values determined in accordance with image SD values for the respective region-specific imaging areas. For reference, a conventional tube current value graph is superimposed and displayed on the left side in FIG. 6A. In addition, when modulation is to be executed, a graph of tube current values determined in accordance with image SDs for the respective region-specific imaging areas is plotted as shown in, for example, FIG. 6B.

Note that on the right side in each of the windows shown in FIGS. 6A and 6B, an image SD value is displayed for each region-specific imaging area, like "image SD-7". The display form of image SDs is not limited to this. For example, information allowing to quantitatively grasp image SDs from the viewpoint of image quality and X-ray dosage may be displayed like "abdominal region high resolution" and "abdominal region low dosage".

The scan controller 30 controls the high-voltage generator 21 in accordance with the tube current values shown in the graph of FIG. 6A, and executes real imaging by a helical scan (step S7).

According to the above arrangement, the following effects can be obtained.

According to this X-ray computed tomography apparatus, an image SD can be set for each imaging region in a scan sequence. Therefore, a large image SD can be set for a region requiring a high-image-quality diagnosis image, while a relatively small image SD can be set for a region which is not especially important for diagnosis. A tube current is determined in accordance with each image SD, and hence a tube current lower than that in the prior art can be set for an area for which a small image SD is set, thereby reducing the exposure to X-rays of the patient.

According to this X-ray computed tomography apparatus, since an image SD can be set for each imaging region in a scan sequence, there is no need to dividedly execute a helical scan for each region. As compared with the case wherein a helical scan is dividedly executed for each region by using the conventional system, reductions in imaging time and operation load can be achieved. This can further reduce the exposure to X-rays of the patient.

The above effects can be explained in the following manner with reference to the views of the accompanying drawing.

Figure 7A:
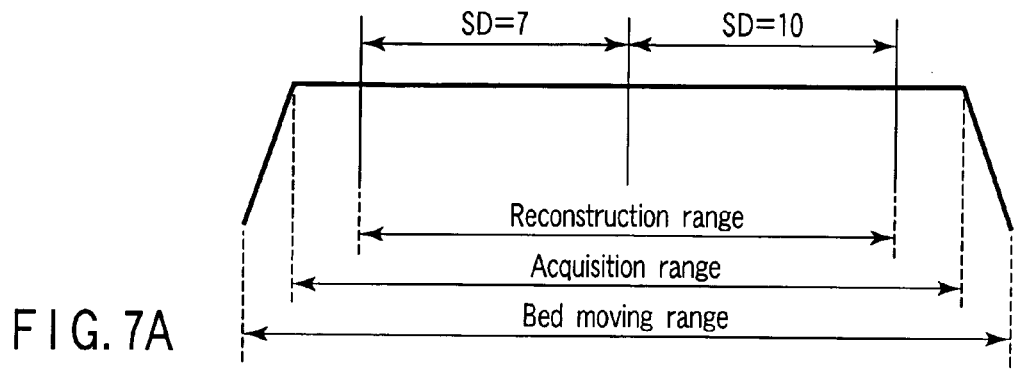
FIG. 7A is a graph showing the relationship between the bed speed and the time when this X-ray computed tomography apparatus sets an image SD for each imaging region and executes one helical scan.
Figure 7B:
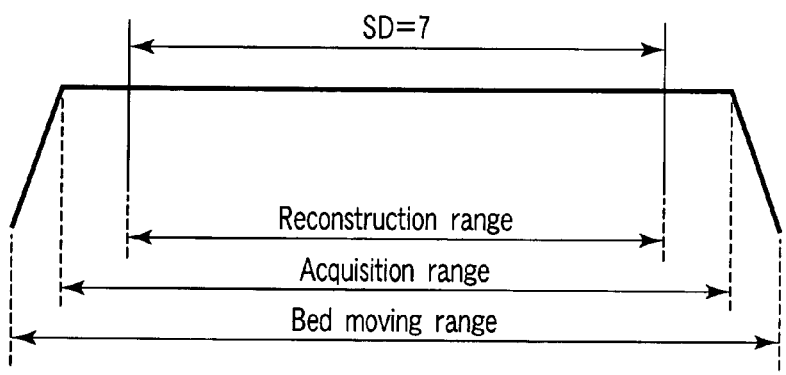
FIG. 7B is a graph showing the relationship between the bed speed and the time when a helical scan is performed for all regions with an image SD (image SD value=10) for a region requiring a high-image-quality diagnosis image.
Figure 7C:
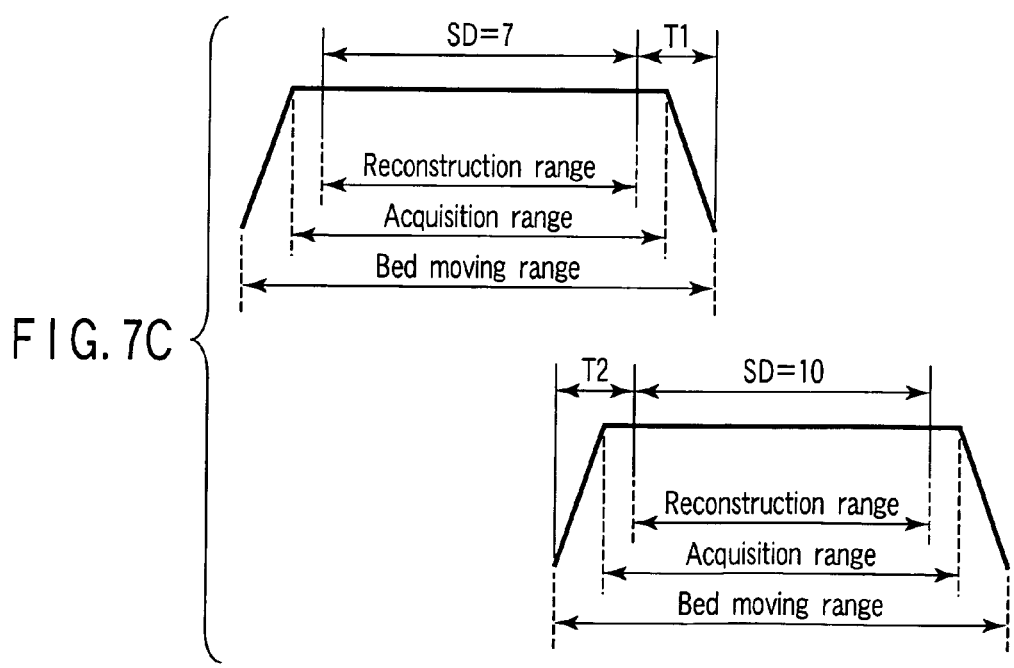
FIG. 7C is a graph showing the relationship between the bed speed and the time when the conventional system divides a helical scan for each region, and sets an image SD for each helical scan.

FIG. 7A is a graph showing the relationship between the bed speed and the time when this X-ray computed tomography apparatus sets an image SD for each imaging region and executes one helical scan. FIG. 7B is a graph showing the relationship between the bed speed and the time when a helical scan is performed for all regions with an image SD (image SD value=7) for a region requiring a high-image-quality diagnosis image. FIG. 7C is a graph showing the relationship between the bed speed and the time when the conventional system divides a helical scan for each region and sets an image SD for each helical scan.

When FIGS. 7A and 7B are compared with each other, in the case shown in FIG. 7B, the image SDs for all the areas are matched with a high-image-quality region. In the case shown in FIG. 7A, the image SD for the first half area (the area with image SD=10) is set to be higher than that for the second half area requiring high image quality. In the first half area in FIG. 7A, therefore, unnecessary exposure to X-rays can be reduced as compared with the case shown in FIG. 7B.

When FIGS. 7A and 7C are compared with each other, in the case shown in FIG. 7C, a helical scan is dividedly executed for each region, and hence the image acquisition range in entire imaging operation is longer than that in the case shown in FIG. 7A. Since X-ray emission is executed in the image acquisition range, intervals T1 and T2 and the like shown in FIG. 7C, for example, correspond to unnecessary exposure to X-rays and operation as compared with the case shown in FIG. 7A.

According to this X-ray computed tomography apparatus, therefore, reductions in imaging time, operation load, and exposure to X-rays of a patient can be achieved as compared with the case wherein the conventional system divides a helical scan for each region and executes each helical scan.

The present invention is not directly limited to the above embodiment, and can be embodied by modifying constituent elements in the execution stage without departing from the spirit and scope of the invention.

For example, in the above embodiment, an X-ray condition is calculated for each imaging region so as to realize an image SD set for each imaging region. However, the present invention is not limited to this. For example, an X-ray condition may be calculated for each imaging region in consideration of, for example, the physique and age of a subject to be examined. Such an arrangement can be implemented by generating tube current patterns in each of which an image SD, physique (body height and weight), age, and X-ray condition are associated with each other, and calculating an X-ray condition for each imaging region by using the patterns.

In addition, various inventions can be formed by proper combinations of a plurality of constituent elements disclosed in the above embodiment. For example, several constituent elements may be omitted from all the constituent elements in the embodiment. Furthermore, constituent elements in different embodiments may be properly combined.

What is claimed is:

1. An X-ray computed tomography apparatus comprising:
an imaging unit which acquires projection data in an arbitrary range in a body axis direction of a subject to be examined by continuously moving a table-top on which the subject is placed and continuously rotating around the subject while exposing X-rays using an X-ray tube;
an image quality level setting unit which sets unique image quality levels for a plurality of areas corresponding to each region of a CT image of the subject;
a calculating unit which calculates an X-ray condition corresponding to a plurality of positions in said each area on the basis of the image quality level; and
a control unit which controls the imaging unit so as to acquire projection data continuously in the each area by exposing X-rays using the X-ray tube in accordance with the X-ray condition, which are obtained by the calculation.

2. An apparatus according to claim 1, wherein the X-ray condition is a tube current value or a tube voltage value of the X-ray tube.

3. An apparatus according to claim 1, wherein the number of the plurality of areas is configured to be arbitrarily set.

4. An apparatus according to claim 1, wherein a size of the each area is configured to be arbitrarily set.

5. An apparatus according to claim 1, which further comprises:
a storage unit in which first X-ray condition information with a CT value being associated with each X-ray condition is stored for each image quality level, and in which
the calculating unit calculates the X-ray condition corresponding to a plurality of positions in the each area on the basis of the CT value of the CT image at each of the plurality of positions in the each area, the set image quality level for the each area and the first X-ray condition information.

6. An apparatus according to claim 1, which further comprises:
an input unit which inputs an age of the subject; and
a storage unit in which second X-ray condition information with each age, and a CT value being associated with each X-ray condition, and each X-ray condition being associated with each other is stored for each image quality level, and in which
the calculating unit calculates the X-ray condition corresponding to a plurality of positions in the each area on the basis of the CT value of the CT image at each of the plurality of positions in the each area, the input age of the subject, the set image quality level for the each area and the second X-ray condition information.

7. An apparatus according to claim 1, wherein the image quality level setting unit performs the setting by using unique image quality levels for the plurality of areas, which are received from another apparatus through a network.

8. An apparatus according to claim 1, further comprising a correcting unit which, when a temporal change in the calculated X-ray condition exceeds an operation limit value of the imaging unit, corrects the calculated X-ray conditions so as not to make the calculated X-ray conditions exceed the operation limit value.

9. An X-ray computed tomography apparatus comprising:
an imaging unit which acquires projection data in an arbitrary range in a body axis direction of a subject to be examined by continuously moving a table-top on which the subject is placed and continuously rotating around the subject while exposing X-rays using an X-ray tube;
a setting unit which sets a unique image SD value for each area obtained by dividing a scanogram of the subject into a plurality of areas corresponding to each region;
a storage unit in which first X-ray condition information with a CT value being associated with each X-ray condition is stored for each image SD value;
a calculating unit which calculates an X-ray condition corresponding to a plurality of positions in the each area on the basis of the CT value of the scanogram at each of the plurality of positions in the each area, the set image SD value for the each area and the first X-ray condition information; and
a control unit which controls the imaging unit so as to acquire projection data continuously in the each area by exposing X-rays using the X-ray tube in accordance with the X-ray condition, which are obtained by the calculation.

10. An apparatus according to claim 9, wherein the X-ray condition is one of a tube current value and a tube voltage value of the X-ray tube.

11. An apparatus according to claim 9, wherein the number of the plurality of areas is configured to be arbitrarily set.

12. An apparatus according to claim 9, wherein a size of the each area is configured to be arbitrarily set.

13. An apparatus according to claim 9, which further comprises:
an input unit which inputs an age of the subject;
a storage unit in which second X-ray condition information with each age, each CT value, and each X-ray condition being associated with each other is stored for each image SD value, and in which
the calculating unit calculates the X-ray condition corresponding to a plurality of positions in the each area on the basis of the CT value of the CT image at each of the plurality of positions in the each area, the input age of the subject, the set image SD value for the each area and the second X-ray condition information.

14. An apparatus according to claim 9, wherein the image SD value setting unit performs the setting by using unique image SD values for the plurality of areas, which are received from another apparatus through a network.

15. An apparatus according to claim 9, further comprising a correcting unit which, when a temporal change in the calculated X-ray condition exceeds an operation limit value of the imaging unit, corrects the calculated X-ray condition so as not to make the calculated X-ray condition exceed the operation limit value.

* * * * *